(12) United States Patent
Ume et al.

(10) Patent No.: US 7,492,449 B2
(45) Date of Patent: Feb. 17, 2009

(54) INSPECTION SYSTEMS AND METHODS

(75) Inventors: Ifeanyi Charles Ume, Atlanta, GA (US);
Lizheng Zhang, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 332 days.

(21) Appl. No.: 11/086,473

(22) Filed: Mar. 22, 2005

(65) Prior Publication Data
US 2005/0225754 A1 Oct. 13, 2005

Related U.S. Application Data

(60) Provisional application No. 60/561,363, filed on Apr. 12, 2004.

(51) Int. Cl.
*G01N 21/00* (2006.01)
(52) U.S. Cl. .................................................. 356/237.1
(58) Field of Classification Search ............... 356/237.1, 356/432; 73/570–671
See application file for complete search history.

(56) References Cited

U.S. PATENT DOCUMENTS

| | | | | |
|---|---|---|---|---|
| 3,671,748 | A * | 6/1972 | Friedman | 250/548 |
| 3,742,439 | A * | 6/1973 | Sheridon | 367/10 |
| 4,554,836 | A * | 11/1985 | Rudd | 73/657 |
| 4,607,341 | A * | 8/1986 | Monchalin | 702/136 |
| 4,641,527 | A * | 2/1987 | Hiroi et al. | 73/582 |
| 5,131,748 | A * | 7/1992 | Monchalin et al. | 356/486 |
| 5,505,090 | A * | 4/1996 | Webster | 73/657 |
| 5,585,921 | A * | 12/1996 | Pepper et al. | 356/487 |
| 5,748,317 | A * | 5/1998 | Maris et al. | 356/502 |
| 5,760,904 | A * | 6/1998 | Lorraine et al. | 356/513 |
| 5,956,143 | A * | 9/1999 | Kotidis | 356/502 |
| 6,182,512 | B1 * | 2/2001 | Lorraine | 73/655 |
| 6,747,268 | B1 * | 6/2004 | Ume | 250/227.11 |
| 2002/0112530 | A1 * | 8/2002 | Kitagawa | 73/61.56 |

OTHER PUBLICATIONS

Paper entitled "Scanned laser Interferometry—4.2.4 Measurement of vibration" pp. 161-164.
Paper entitled "Solder Joints 13.39—Low-Cycle Fatigue" 1 page.
Paper entitled "12.9 Correlation Analysis" pp. 657-662.
Article entitled "Survey of non-destructive inspection methods for solder joint integrity." by O'Conchuir et al., IEEE 1991, pp. 1268-1275.
Article entitled "Ultrasound generation in single-crystal silicon using a pulsed Nd: YAG laser" by S. Dixon, et al., © 1996 IOP Publishing Ltd., pp. 1345-1348.

(Continued)

*Primary Examiner*—Tarifur R. Chowdhury
*Assistant Examiner*—Isiaka O Akanbi
(74) *Attorney, Agent, or Firm*—Thomas, Kayden, Horstemeyer & Risley, LLP

(57) ABSTRACT

Embodiments of inspection systems and methods are disclosed. One embodiment of an inspection system, among others, comprises logic configured to receive a reference signal and a target signal, the reference signal having first surface displacement information and the target signal having second surface displacement information, said logic configured to determine a correlation coefficient between the first surface displacement information and the second surface displacement information, the correlation coefficient indicating whether an inspected object exhibits a defect.

22 Claims, 7 Drawing Sheets

OTHER PUBLICATIONS

Article entitled "A Novel Approach for Flip Chip Solder Joint Quality Inspection: Laser Ultrasound and Interferometric System", by Liu et al., IEEE Transactions on Components and Packaging Technologies, vol. 24, No. 4, Dec. 2001, pp. 616-624.

Article entitled "Capabilities of Flip Chip Defects Inspection Method by Using Laser Techniques" by Liu et al., The International Journal of Microdircuts and Electronic Packaging, vol. 24, No. 2, 2nd Quarter, 2001, pp. 122-131.

Article entitled "Online-Offline Laser Ultrasonic Quality Inspection Tool for Multi-Layer Chip Capacitors" by Erdahl et al., 2002 Electronic Components and Technology Conference, pp. 225-231.

Article entitled "Inspection of Flip Chip and Chip Scale Package Interconnects Using Laser Ultrasound and Interferometric Techniques" by Howard et al., The International Journal of Microcircuits and Electronic Packaging, vol. 25, No. 1, 1st Quarter, 2002, pp. 1-14.

Paper entitled "CEM CEX 2003—Selection Criteria for X-ray Inspection Systems for BGA and CSP Solder Joint Analysis" by Joachim Gudat Dage Semiconductor GmbH, pp.1-9.

Article entitled "Vibration Analysis Based Modeling and Defect Recognition for Flip-Chip Solder-Joint Inspection" by Liu et al., Journal of Electronic Packaging, Sep. 2002, vol. 124, pp. 221-226.

Article entitled "Digital Signal Processing in a Novel Flip Chip Solder Joint Defects Inspection System" by Liu et al., Journal of Electronic Packaging, Mar. 2002, vol. 125, pp. 39-43.

Article entitled "Flip Chip Process Challenges for SMT Assembly" by Craig Beddingfield, Siemens Dematic Electronics Assembly Systems, Mar. 1, 2003, 5 pages.

Article entitled "Defects Pattern Recognition for Flip-Chip Solder Joint Quality Inspection with Laser Ultrasound and Interferometer" by Sheng Liu, IEEE Transactions on Electronics Packaging Manufacturing, vol. 27, No. 1, Jan. 2004, pp. 59-66.

* cited by examiner

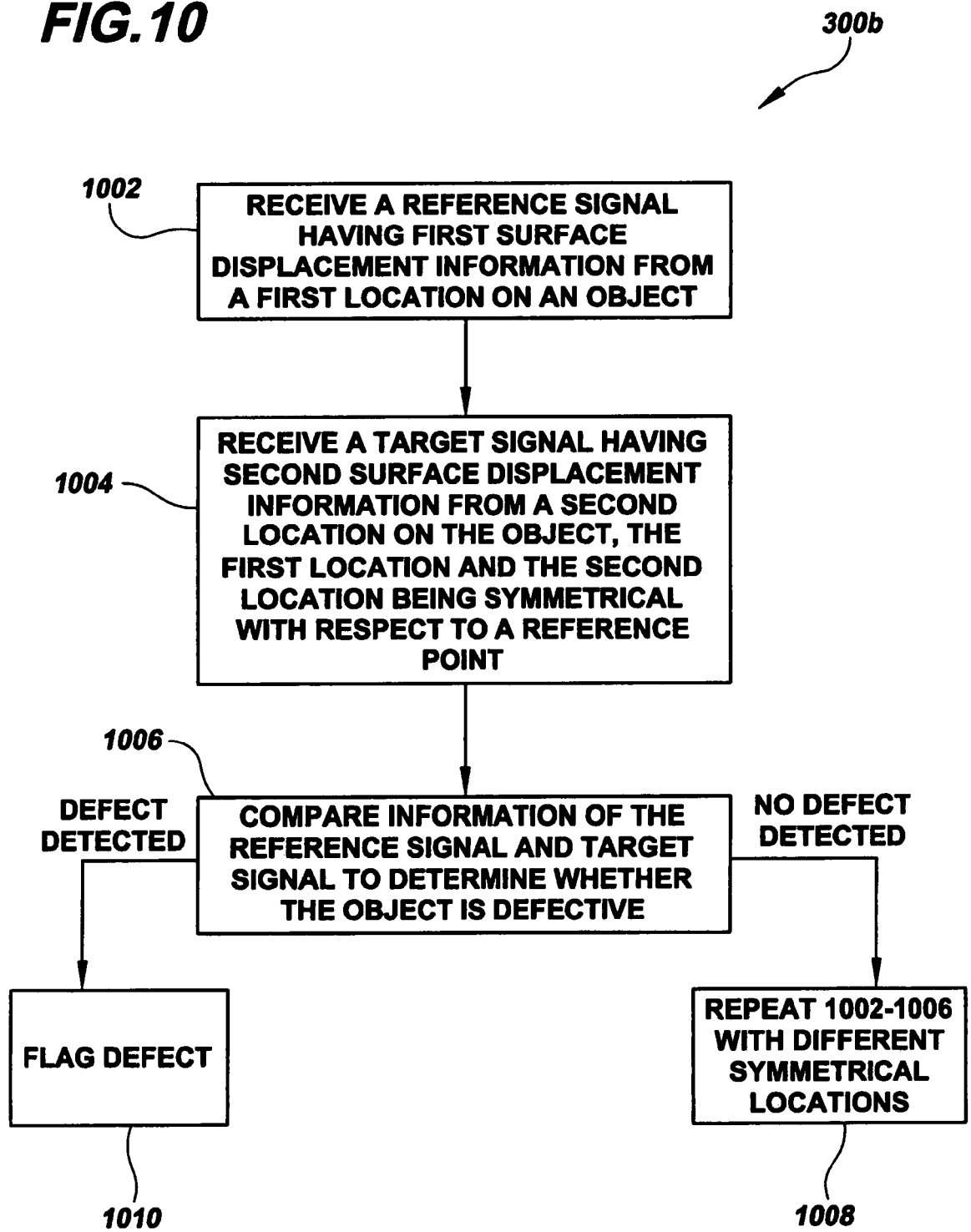

INSPECTION SYSTEMS AND METHODS

CROSS-REFERENCE TO RELATED APPLICATION

This application claims the benefit of U.S. Provisional Application No. 60/561,363, filed Apr. 12, 2004, which is entirely incorporated herein by reference.

STATEMENT REGARDING FEDERALLY SPONSORED RESEARCH OR DEVELOPMENT

The U.S. government may have a paid-up license in this invention and the right in limited circumstances to require the patent owner to license others on reasonable terms as provided for by the terms of DMI-0217311 awarded by the National Science Foundation of the U.S.

TECHNICAL FIELD

The present invention is generally related to inspection systems, and in particular, non-destructive solder joint inspection systems and methods.

BACKGROUND

Computer chips are typically connected to computer boards, such as printed circuit boards (PCB's), by soldering. For instance, conventional computer chips have been connected to such boards in the past by soldering a plurality of pins extending from the chip to the board. Presently, consumer demands are driving the current trend in the electronics industry to make products that are compact, high in density, light, and thin. These demands have created new chip inter-connection methods. One such inter-connection method is known as solder bump or ball technology. Flip chip, ball grid arrays, chip scales, and multi-chip modules each use small solder bumps underneath the chips for interconnection, typically making them superior in performance to other more conventional interconnection technologies.

The standard flip chip assembly process in a surface mount technology environment, for example, includes the following steps: flux application, die placement, solder reflow, and underfill processing. Once a defect is found in the flip chip connection after underfilling, the whole circuit board usually has to be discarded, since reworking underfilled flip chips is complicated and costly. Therefore, it is desirable to have an inspection process between the solder reflow and underfill dispensing processes to reduce the manufacturing cost.

Among various solder joint defects, detection of solder joint cracks remains a challenge to available automated non-destructive inspection techniques, such as Automated Optical Inspection (AOI), Acoustic Microscopy Imaging (AMI), and Automated X-ray Inspection (AXI). Solder joints with cracks often have intermittent connections and they often can pass functional tests or in-circuit tests, but may cause problems during normal operations. Flip chip solder joints are hidden from direct view and are difficult to access with automated optical inspection equipment. Both AMI and AXI are able to generate penetrative images, but both methods have difficulties in imaging cracks, especially cracks in the vertical direction (i.e., the direction perpendicular to the imaging plane). 3D X-ray laminography techniques used in AXI are capable of identifying defects in the vertical direction. However, these techniques are generally not suitable for in-line inspection because of their slow throughput and the complicated image interpretation algorithms necessary to evaluate the data. In addition, both AMI and AXI systems usually have high operating and equipment costs.

SUMMARY

Embodiments of inspection systems and methods are provided. Briefly described, one embodiment of an inspection system, among others, comprises logic configured to receive a reference signal and a target signal, the reference signal having first surface displacement information and the target signal having second surface displacement information, said logic configured to determine a correlation coefficient between the first surface displacement information and the second surface displacement information, the correlation coefficient indicating whether an inspected object exhibits a defect.

Embodiments of inspection methods are also provided. In this regard, one embodiment of an inspection method, among others, comprises receiving a reference signal having first surface displacement information, receiving a target signal having second surface displacement information, and determining a correlation coefficient between the first surface displacement information and the second surface displacement information, the correlation coefficient indicating whether an inspected object exhibits a defect.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of inspection systems and methods can be better understood with reference to the following drawings. The components in the drawings are not necessarily to scale, emphasis instead being placed upon clearly illustrating the principles of the present systems and methods. Moreover, in the drawings, like reference numerals designate corresponding parts throughout the several views.

FIG. 10 is a flow diagram that illustrates an embodiment of an auto comparison method.

DETAILED DESCRIPTION OF THE PREFERRED EMBODIMENTS

Figure 1:
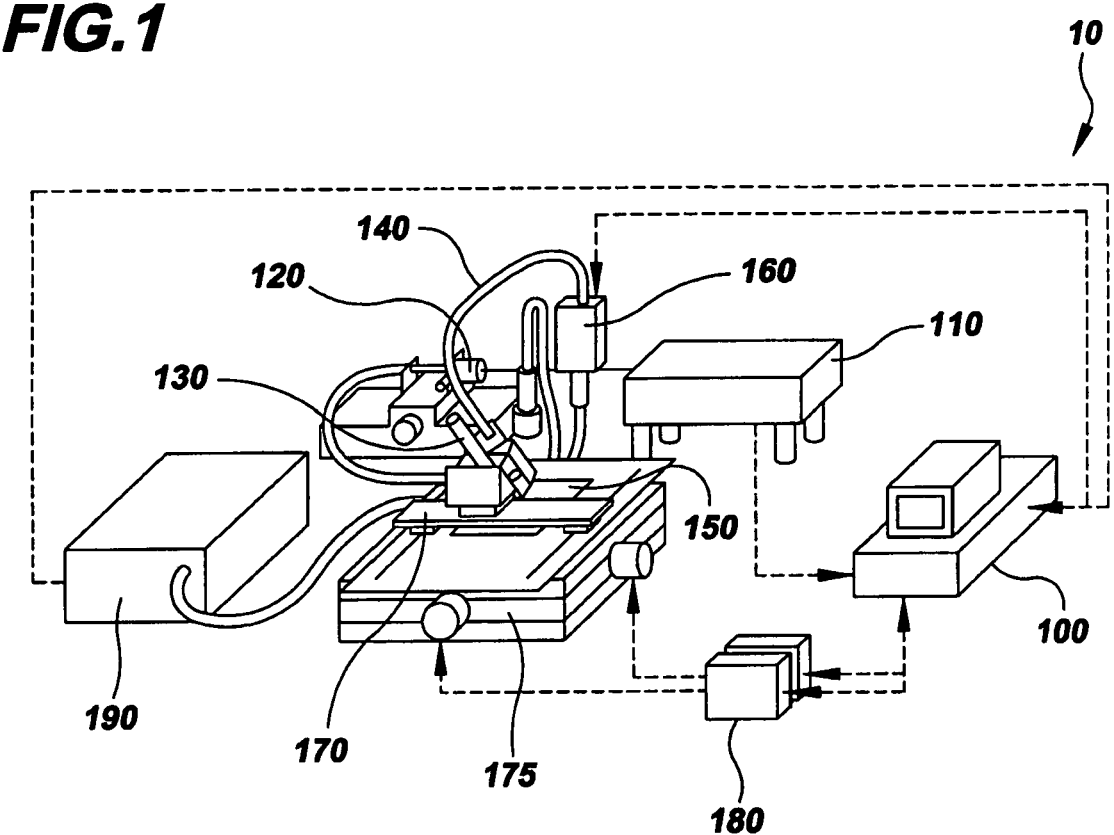
FIG. 1 is a schematic diagram of an example environment for an embodiment of an inspection system.

Disclosed herein are various embodiments of inspections systems and methods (herein, inspection systems for brevity). Such inspection systems can be understood in the context of a test/evaluation system. Inspection systems may be implemented in low-cost, highly-sensitive, highly-automated test/evaluation systems to perform solder joint and electronics component quality evaluations. A fully developed test/evaluation system can be placed in-line for production inspection or off-line as a nondestructive failure analysis tool. An inspection method may utilize one or more algorithms (e.g., error ratio analysis, correlation coefficient and/or a derivative thereof, etc.) to analyze ultrasound signals and surface displacement signals, and can also be added into a feature vector when implementing defect pattern recognition.

In one embodiment, a laser ultrasound and vibrometer system induces sound waves in a semiconductor chip and detects the surface displacement(s) resulting from the induced sound waves. An inspection system receives signals from the ultrasound and vibrometer system, the signals including information about surface displacement of the semiconductor chip. Such an inspection system may also receive a reference signal that may be derived from the same semiconductor chip (e.g., in the case of symmetrical solder bumps, as explained below) or from another reference semiconductor chip that is known to have no defects in its corresponding solder joints. The inspection system may be configured to process the received signals using time-domain error ratio analysis, frequency-domain spectral analysis, defect pattern recognition methods, and/or preferably correlation coefficient analysis or a derivative thereof to inspect for solder joint defects (e.g., thermal cycle induced cracks in flip chip solder joints). Detection of surface displacement(s) preferably occurs at optimum detection locations on the chip surface. In this regard, an inspection system according to the preferred embodiments can be placed in-line and serve as a low-cost go/no-go inspection tool to screen out defects in solder joints at an early stage in the manufacturing process. Additionally, an inspection system may have application in the development process (e.g., laboratory applications).

Although described in the context of solder joint inspection in flip-chips attached to printed wiring boards (PWBs) or printed circuit boards (PCBs), it will be understood in the context of this disclosure that the scope of this disclosure includes other interconnect bump or joint technology, as well as systems where components or devices are connected to a surface with solder or other interconnect materials.

Also covered by this disclosure are systems and methods that provide for the inspection of other features and components such as electronic packages, board cracks, missing bumps, misalignments, etc. Other capabilities considered within the scope of this disclosure include the inspection of leadless surface mount components, such as flex cracks in multi-layer chip capacitors, among other capabilities.

FIG. 1 is a schematic diagram of an example test/evaluation system 10, which incorporates an embodiment of an inspection system. The test/evaluation system 10 includes a processing device 100 (e.g., computer, signal processing chip, etc.), a laser 110, a laser input coupler 120, a laser focus stage 130, one or more fiber optic cables 140, a printed circuit board (PCB) 150 having one or more objects (e.g., components) that are soldered to the PCB 150, a vision sensor 160, a computer driven movement stage 175 upon which the PCB 150 is positioned, a manual movement stage 170 that is disposed on movement stage 175 for adjusting the location of the laser excitation point, motor controllers 180 that positions the movement stage 175, and a vibrometer 190 that detects surface displacement (e.g., chip surface displacement) resulting from ultrasonic waves induced by the laser 110. The movement stage 175 is used to translate the PCB 150 with reference to the vibrometer 190, which in one embodiment has a fixed position. By translating the PCB 150, different objects and locations on the PCB 150 can be inspected. In some embodiments, the stages 170 and 175 can be integrated together. In one embodiment, the laser 110 may be a pulsed Nd:YAG laser, which is used as the excitation source to induce ultrasonic waves. Excitation by nanosecond (ns) scale laser pulses causes nearly instantaneous heating and material strain on an object (e.g., semiconductor chip) disposed on the PCB 150, producing broadband ultrasonic waves from the kilohertz (kHz) to megahertz (MHz) range.

The laser input coupler 120 couples the laser pulses provided by the laser 110 to the fiber optic cable 140. The fiber optic cable 140 directs the laser pulses to objects on the PCB 150. Although shown using a single fiber optic cable 140, additional fiber optic cables may be used to induce surface displacement, particularly for larger objects on the PCB 150. Beam focus is adjusted using the laser focus stage 130. The stage 170 may be positioned to enable the laser pulses to impinge on various objects located on the PCB 150. Movement of the stage 170 is manually controlled and independent from the movement stage 175, which is controlled by the processing device 100. The processing device 100 provides actuation signals to the motor controllers 180. In some embodiments, the position of the laser may be moved alone or in cooperation with the stages 170 and 175.

The vibrometer 190 may be configured as a laser Doppler vibrometer, which measures the out-of-plane surface vibrations induced by the laser pulses. The vibrometer 190 senses changes in the phase of laser light scattered from a vibrating surface of an object on the PCB 150 and provides a voltage signal (or current signal in some embodiments) proportional to instantaneous surface displacements. The vibrometer 190 may include a filter (not shown), which can limit the signal bandwidth to two different pass-bands. For example, signals may be limited to a pass-band from approximately 25 kHz to approximately 2 MHz., which enables a resolution of approximately 0.07 nanometers (nm). A second pass-band may range from approximately 25 kHz to approximately 20 MHz, which can be used for wider band signal measurements.

Figure 2:
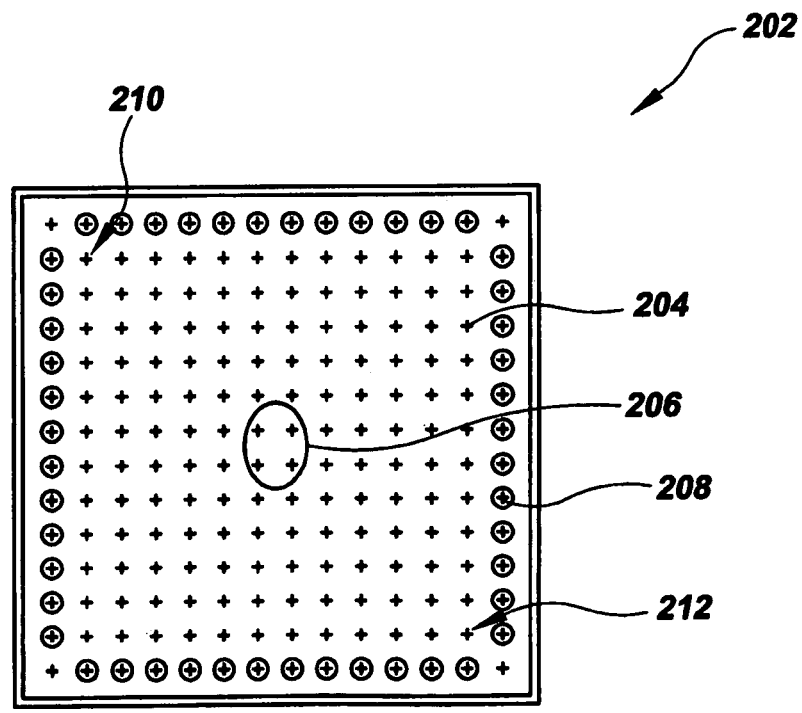
FIG. 2 is a schematic diagram of an exemplary object to be tested by the inspection system shown in FIG. 1.

FIG. 2 is a schematic diagram of an exemplary object (e.g., semiconductor chip) 202 that may be disposed on the PCB 150 (FIG. 1). The object 202 is shown with diagrammatic representations of exemplary inspection points 204 implemented by the vibrometer 190 (FIG. 1). The inspection points 204 are configured in a 14×14 pattern, as shown by way of illustration and not limitation. The object 202 is also shown with a diagrammatic representation of a laser excitation spot 206, represented here in elliptical fashion, although not limited to such a geometry. It will be understood that the spot 206 may impinge on other areas of the object 202, and/or additional spots (e.g., through use of additional fiber optic cables 140, FIG. 1, for example) may be used. The object 202 includes solder bumps 208 located at least along the periphery of the object 202. In one embodiment, the solder bumps 208 (represented using circles) are arranged in symmetrical fashion with respect to a reference point (e.g., the physical center of the object 202), such that an inspection location 210 has a mirror image location 212. Other bump patterns and other inspection location symmetry may be used. The 14×14 points inspection pattern is preferably selected so that the pitch (i.e., center-to-center distance) of the inspection points 204 is the same as the solder bump pitch, and each solder bump 208 has an inspection point 204 right on top of it. This exemplary scanning inspection pattern gives detailed information of the vibration response of the objects' whole surface.

In some implementations, the 14×14 scanned inspection points 204 in FIG. 2 may provide more information than necessary to evaluate an object's solder joints. By choosing optimum inspection locations in some embodiments, fewer (e.g., two) inspection points may be enough for processing. Average modified correlation coefficients (MCCs) (explained below) for inspection points collected at different distances from the center of a chip were collected using a test setup as described below. When comparing defective target chips (on target panels) with a reference chip (chip or chips with no defects on reference panels), it was revealed that the closer the inspection points were to the chip edge (at or near solder bump locations), the higher the MCC values are. However, the closer the inspection points were to the chip center (e.g., in proximity to the shown excitation point 206), the smaller the MCC values. For a comparison between two reference chips, the MCC values vary in the same pattern but in a much smaller range. These observations indicate that the locations closer to the solder joints are the optimum choices for inspection. Analyses have shown that by using the data collected on the four corners of the chip may be enough to evaluate the chip's solder joint quality using a MCC method, ER method, among other methods.

Figure 3:
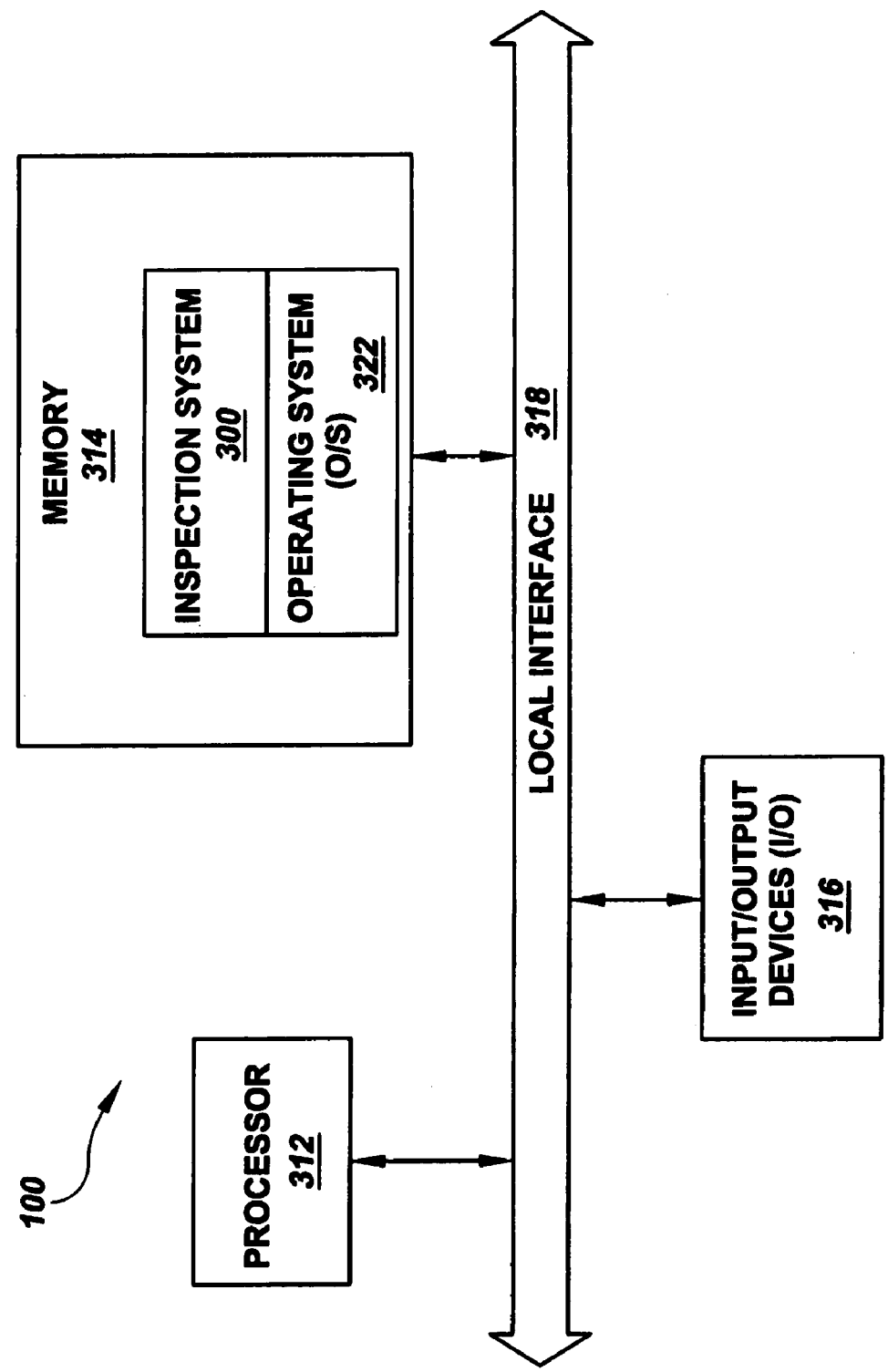
FIG. 3 is a block diagram showing a configuration of a processing device that can implement an embodiment of an inspection system.

FIG. 3 is a block diagram showing a configuration of the processing device 100 incorporating an inspection system. In FIG. 3, an inspection system is denoted by reference numeral 300. In some embodiments, an inspection system may comprise one or more components of the processing device 100, among other components. Generally, in terms of hardware architecture, the processing device 100 includes a processor 312, memory 314, and one or more input and/or output (I/O) devices 316 (or peripherals) that are communicatively coupled via a local interface 318. The local interface 318 may be, for example, one or more buses or other wired or wireless connections. The local interface 318 may have additional elements such as controllers, buffers (caches), drivers, repeaters, and receivers, to enable communication. Further, the local interface 318 may include address, control, and/or data connections that enable appropriate communication among the aforementioned components.

The processor 312 is a hardware device for executing software, particularly that which is stored in memory 314. The processor 312 may be any custom made or commercially available processor, a central processing unit (CPU), an auxiliary processor among several processors associated with the processing device 100, a semiconductor-based microprocessor (in the form of a microchip or chip set), a macroprocessor, or generally any device for executing software instructions.

The memory 314 may include any one or combination of volatile memory elements (e.g., random access memory (RAM)) and nonvolatile memory elements (e.g., ROM, hard drive, etc.). Moreover, the memory 314 may incorporate electronic, magnetic, optical, and/or other types of storage media. Note that the memory 314 may have a distributed architecture in which where various components are situated remotely from one another but may be accessed by the processor 312.

The software in memory 314 may include one or more separate programs, each of which comprises an ordered listing of executable instructions for implementing logical functions. In the example of FIG. 3, the software in the memory 314 includes the inspection system 300 according to one embodiment and a suitable operating system (O/S) 322. The operating system 322 essentially controls the execution of other computer programs, such as the inspection system 300, and provides scheduling, input-output control, file and data management, memory management, and communication control and related services.

The inspection system 300 is a source program, executable program (object code), script, or any other entity comprising a set of instructions to be performed. The inspection system 300 can be implemented, in one embodiment, as a distributed network of modules, where one or more of the modules can be accessed by one or more applications or programs or components thereof. In some embodiments, the inspection system 300 can be implemented as a single module with all of the functionality of the aforementioned modules. When the inspection system 300 is implemented as a source program, then the program is translated via a compiler, assembler, interpreter, or the like, which may or may not be included within the memory 314, so as to operate properly in connection with the O/S 322. Furthermore, the inspection system 300 can be written with (a) an object oriented programming language, which has classes of data and methods, or (b) a procedure programming language, which has routines, subroutines, and/or functions, for example but not limited to, C, C++, Pascal, Basic, Fortran, Cobol, Perl, Java, and Ada.

The I/O devices 316 may include input devices such as, for example, a keyboard, mouse, scanner, microphone, etc. Furthermore, the I/O devices 316 may also include output devices such as, for example, a printer, display, etc. Finally, the I/O devices 316 may further include devices that communicate both inputs and outputs such as, for instance, a modulator/demodulator (modem for accessing another device, system, or network), a radio frequency (RF) or other transceiver, a telephonic interface, a bridge, a router, etc.

When the processing device 100 is in operation, the processor 312 is configured to execute software stored within the memory 314, to communicate data to and from the memory 314, and to generally control operations of the processing device 100 pursuant to the software. The inspection system 300 and the O/S 322, in whole or in part, but typically the latter, are read by the processor 312, perhaps buffered within the processor 312, and then executed.

When the inspection system 300 is implemented in software, as is shown in FIG. 3, it should be noted that the inspection system 300 can be stored on any computer-readable medium for use by or in connection with any computer-related system or method. In the context of this document, a computer-readable medium is an electronic, magnetic, optical, or other physical device or means that can contain or store a computer program for use by or in connection with a computer related system or method. The inspection system 300 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In an alternative embodiment, where the inspection system 300 is implemented in hardware, the inspection system 300 can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc; or can be implemented with other technologies now known or later developed.

Figure 4:
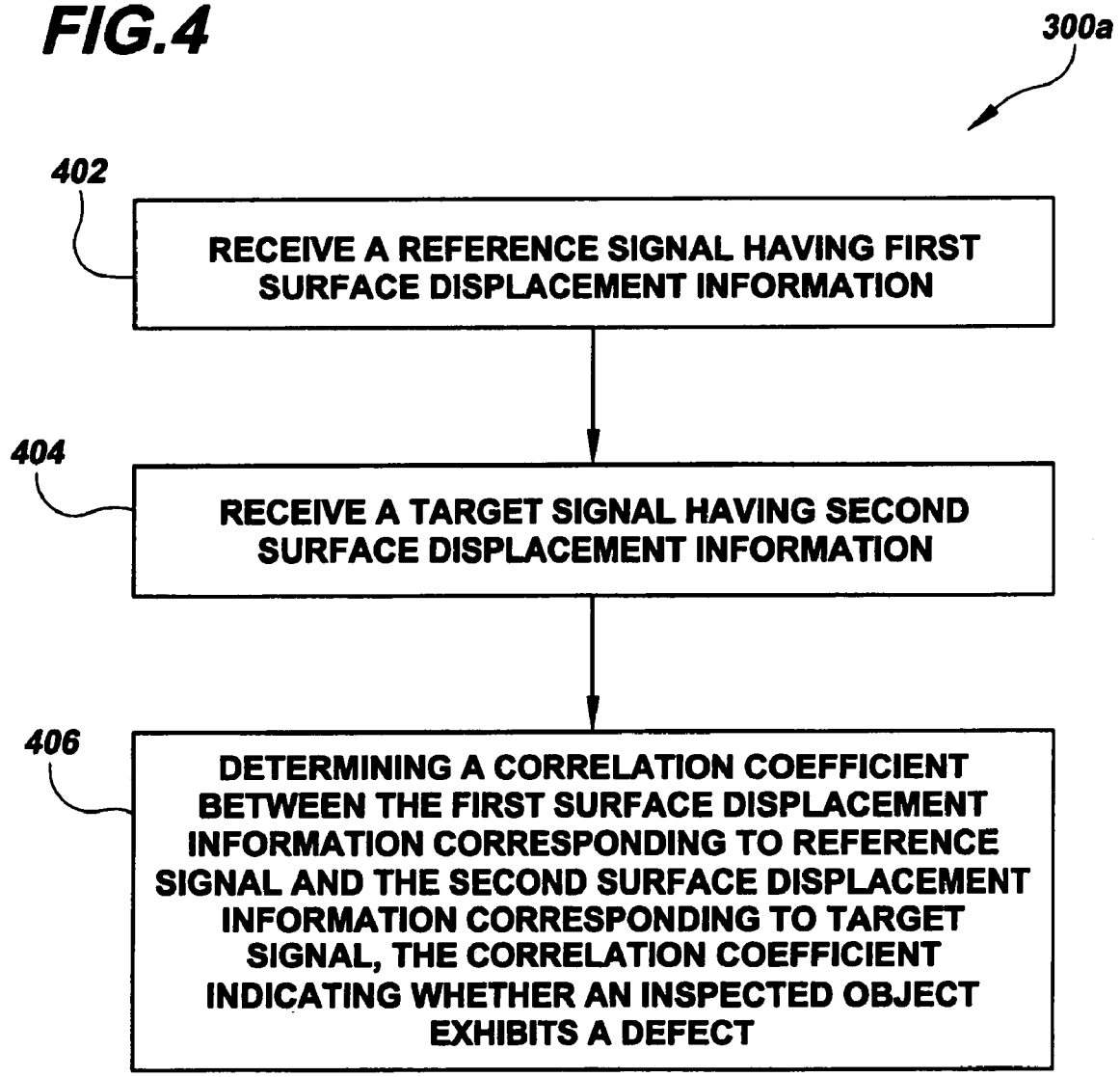
FIG. 4 is a flow diagram that illustrates an inspection method embodiment.

FIG. 4 is a flow diagram of one method embodiment 300a the inspection system 300 can use to inspect one or more objects. FIGS. 5-7B are various plots that will be used in conjunction with the discussion of the flow diagram of FIG. 4. In particular, the plots in FIGS. 5-7B represent the results of a test set-up that is described briefly below. Further information about the test set-up can be found in the provisional from which this disclosure is based. A test device was provided that included a daisy chain flip chip test die with 48 eutectic solder bumps (24 daisy chain pairs) around the perimeter of the device. The device size was 6.35 millimeters (mm) ×6.35 mm and the typical solder bump diameter was 190 micrometers (μm) with a bump pitch of 457 μm. The chips were surface mounted and reflowed without underfill together with other surface mount devices. Each panel had six board units, and each board had three chips. Five such panels were electrically tested to make sure all 90 flip chips mounted on them had good connections. Then, three panels were kept as references and the other two panels were put through air-to-air temperature cycling using condition G of the JEDEC standard JESD22-A104-B, with a temperature range from −40° Celsius (° C.) to 125° C. The dwell time at both high and low temperatures was 30 minutes. Cracks generally initiate and grow within solder joints during thermal cycling due to coefficient of thermal expansion (CTE) mismatch. For flip chips without underfill, these cracks grow faster and eventually lead to the failure of the solder joint connections. After 100 thermal cycles, all the chips failed in the electrical test, indicating that cracked solder joints occurred. The three reference panels were named R1, R2, and R3, respectively, and the two thermal cycled panels were named A1 and A2, respectively.

X-ray analysis was performed before laser ultrasound testing. The equipment used for X-ray analysis was a nanofocus inspection system, which offered micrometer defect detection capabilities. The X-ray system had a five-axes control for precise sample positioning at different angles. X-ray images of the reference chip and of a defective chip revealed very few differences between the reference chip and the thermal cycled chip. The images, including oblique views, were unable to show any evidence of cracks, and essentially revealed a few images of voids in a localized area of the chip.

The setup was implemented using the test/evaluation system 10 shown in FIG. 1, and thus will herein be described with reference to the test/evaluation system 10. The test/detect system 10 included the laser 110 configured as a pulsed Nd:YAG laser, with an operating wavelength of 1064 nm and a 20 Hertz (Hz) pulse repetition rate. The laser 110 was capable of generating pulses with a width on the order of 4~5 ns with the maximum pulse energy of 45 milli-Joules (mJ), which can be adjusted by a motorized optical attenuator incorporated in the laser 110 (FIG. 1) but not shown. The fiber optic cable 140 was used to launch optical energy onto the sample (e.g., object 202, FIG. 2) with an angle of illumination of 45°. The 45° angle allows the interferometer (of the laser vibrometer 190) to be positioned perpendicular to the object surface to access any point on the surface. Other angles of illumination may be used. Before each experiment, the laser output power was measured and tuned at the output end of the fiber optic cable 140. In the set-up experiments, 70 milli-Watt (mW) average power was used, which corresponds to a pulse energy of 3.5 mJ/pulse at the 20 Hz repetition rate. An elliptical excitation spot, similar to that shown in FIG. 2 (e.g., excitation laser spot 206), had an area of about 2.5 mm2, giving an approximate energy density of 0.14 Joules-per-centimeters-squared (J/cm2). Ultrasonic waves in the thermoelastic regime were generated in the experiments.

The vibrometer 190 was used to measure the out-of-plane surface displacements at selected inspection points, such as represented by inspection point 204 of FIG. 2. For a single inspection point, multiple measurements were taken at consecutive laser pulses and averaged to suppress signal noise. The analog output signal of the vibrometer 190 was sampled at 25 MHz with a data acquisition card, such as would be implemented in the processing device 100 (FIG. 1). The pulse duration was about 4~5 ns and data was typically acquired during a period of approximately 160 μs. The vision sensor 160 was used to locate the circuit board fiducials, and the processing device 100 calculated the excitation and detection coordinates and drove the movement stage 175 (FIG. 1). The movement stage 175, as explained above, positioned the test device (e.g., PCB 150, FIG. 1) under the vibrometer probe (also known as an interferometer) for measurement at selected points (e.g., inspection points 204). The positioning repeatability of the stage 170 was approximately ±6 μm and ±4 μm in the X and Y axis, respectively. The laser excitation point (e.g., 206, FIG. 2) was positioned by a manual stage 170 affixed to the top of the stage 175. The manual stage 170 uses preloaded linear motion components and linear encoders (not shown) for precision positioning, and the overall stage precision was estimated to be better than ±10 μm in each axis. The PCB 150 was held by a vacuum fixture during the experiments.

It should be understood that any process descriptions or blocks in flow diagrams shown in FIG. 4 and FIG. 10 should be understood as representing modules, segments, or portions of code which include one or more executable instructions for implementing specific logical functions or steps in the process, and alternate implementations are included within the scope of the preferred embodiments in which functions may be executed out of order from that shown or discussed, including substantially concurrently or in reverse order, depending on the functionality involved, as would be understood by those reasonably skilled in the art.

Figure 5:
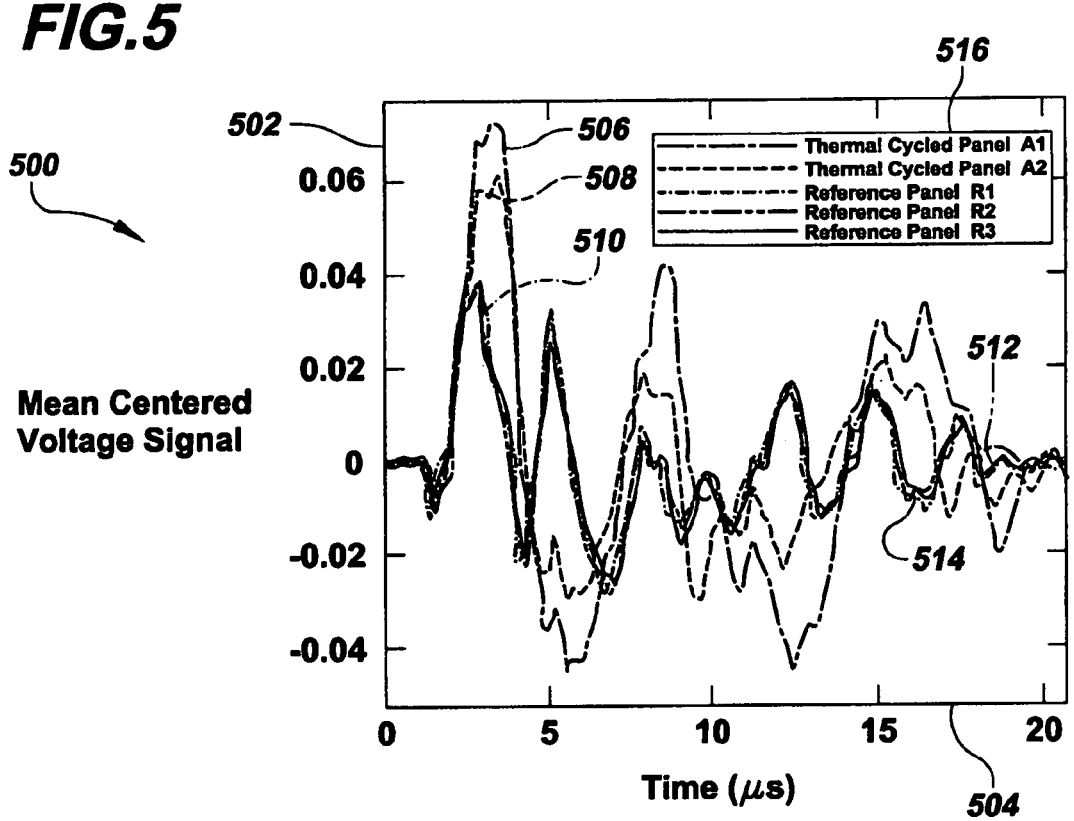
FIG. 5 is a plot that illustrates waveforms of surface displacement signals collected from a test panel.

With reference to FIG. 4, block 402 of the method 300a includes receiving a reference signal having first surface displacement information, and block 404 includes receiving a target signal having second surface displacement information. FIG. 5 is a signal plot 500 of a waveform of signals collected from a test panel. Signal plot 500 includes a vertical or y-axis 502, and a horizontal or x-axis 504. The y-axis 502 represents the mean centered voltage signal in units of volts, and the x-axis 504 represents the time or duration in units of seconds for signal waveforms (explained below) to diminish to approximately zero volts. Waveforms 506 and 508 correspond to target signals from a first panel (A1) and a second panel (A2), respectively, of the test panel. Waveforms 510, 512, and 514 correspond to reference signals from a first reference panel (R1), second reference panel (R2), and third reference panel (R3), respectively. The waveforms 506-514 have the representations shown in ledger 516. The waveforms 506-514 were collected from a single point on five different boards. These signals were collected from the same chip location on each panel in order to minimize positional variations. As shown, the waveforms 510-514 of the three reference signals match each other well, while the other two waveforms 506 and 508 corresponding to thermally cycled samples deviate from the reference signals.

Figure 6:
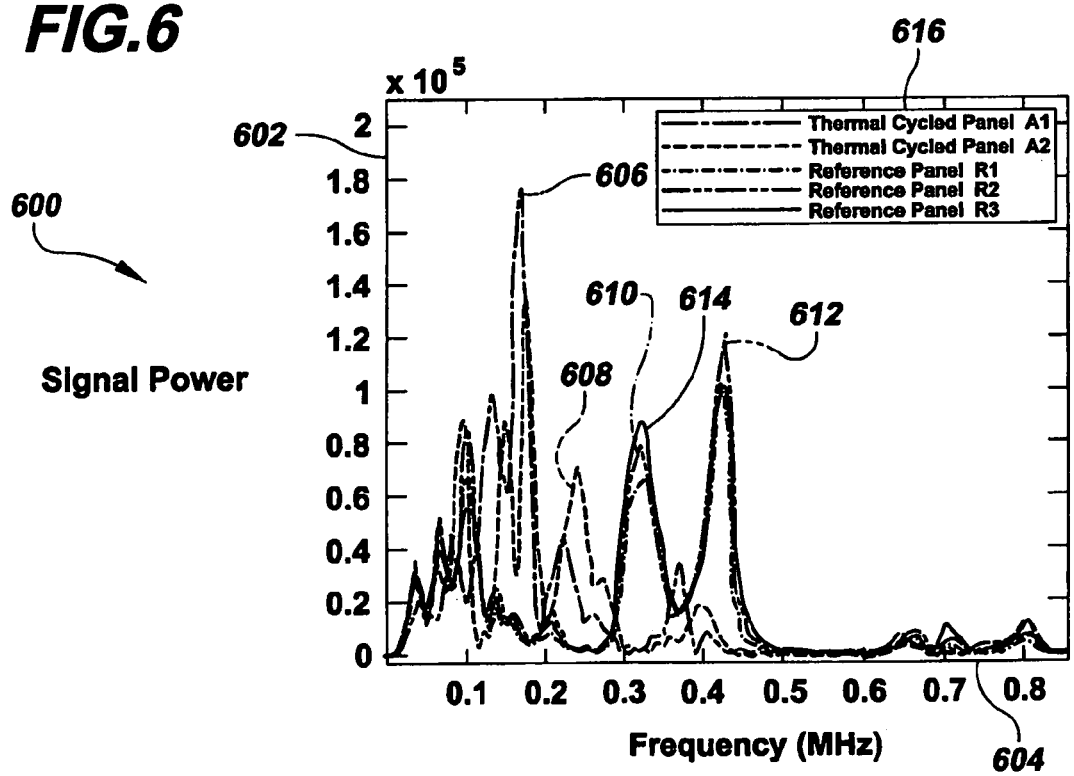
FIG. 6 is a plot that illustrates power spectra corresponding to the signal waveforms shown in FIG. 5.

The power spectra of these signals are shown in FIG. 6. In particular, signal plot 600 has y-axis 602 corresponding to signal power and reveals relative amplitudes, an x-axis 604 corresponding to frequency (in units of MHz), and a ledger

616. Power spectra 606 and 608 correspond to thermally cycled samples as indicated in FIG. 5, and power spectra 610-614 correspond to reference samples. As illustrated, the power spectra 606-614 show the same relationship as the waveforms 506-514. Furthermore, the signal peak amplitudes corresponding to thermal cycled samples (606 and 608) are higher than those corresponding to the reference samples (610-614). Also, the resonant frequencies corresponding to thermally cycled samples (606 and 608) are lower than those corresponding to the reference samples (610-614). These phenomenon indicate weaker interconnections in thermally-cycled chips.

With reference to FIG. 4, block 406 includes determining a correlation coefficient between the first surface displacement information corresponding to the reference signal and the second surface displacement information corresponding to the target signal, the correlation coefficient indicating whether an inspected object exhibits a defect. Investigation of scatterplots of the signal waveforms of FIG. 5 indicate that signals obtained from different reference samples have some extent of linear dependence, whereas signals from the reference and defective samples are substantially independent. This linear relationship between two reference signals forms the basis for the correlation coefficient calculation. Note that in some embodiments, the inspection system 300 (FIG. 3) may be configured to provide alternatives or supplements to the correlation coefficient analysis. For example, during evaluation, or at other periods of test/evaluation, a user prompt may be provided on a computer display that provides a user with selectable options that include the correlation coefficient, error ratio (ER) method, among others.

The correlation coefficient, r, can be calculated by the following equation:

$$r = \frac{\sum_n (R_n - \overline{R})(A_n - \overline{A})}{\sqrt{\left(\sum_n (R_n - \overline{R})^2\right)\left(\sum_n (A_n - \overline{A})^2\right)}} \quad \text{Eq. 1}$$

where Rn is the reference signal, $\overline{R}$ is the mean of Rn, An is the signal to be compared with Rn, $\overline{A}$ is the mean of An. In one embodiment, A and R comprise vibration amplitude measurements in volts, each vector comprising a series of surface displacement amplitudes varying with time. The correlation coefficient is a scalar value, which lies between −1 and 1. The correlation coefficient represents a normalized measure of the strength of the linear relationship between two vectors. A value of r equal to 1 indicates that the two vectors Rn and An correlate positively and perfectly. If on the other hand the two vectors vary oppositely and perfectly, r is equal to −1. If the two vectors vary independently, then r is equal to 0. Since the ER method gives larger values when the differences between two signals are large, and since some embodiments may provide the correlation coefficient and error ratio (ER) method as selectable options, the correlation coefficient results may be made consistent with those of ER by using a modified correlation coefficient. A modified correlation coefficient limits the result in the range of 0 to 1. Thus, a modified correlation coefficient, $(1-r^2)$, can be used in inspection analysis instead of r. Thus, when $(1-r^2)$ equals 1, the two signals are independent, and when $(1-r^2)$ is close to or equal to 0, the two signals have strong linear dependence.

Figure 7A:
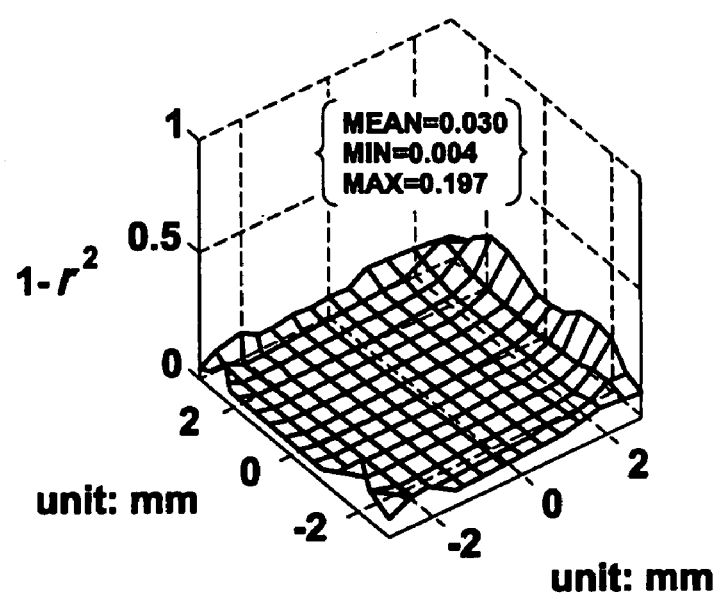
FIG. 7A is a plot that illustrates modified correlation coefficient analysis results of two reference chips.
Figure 7B:
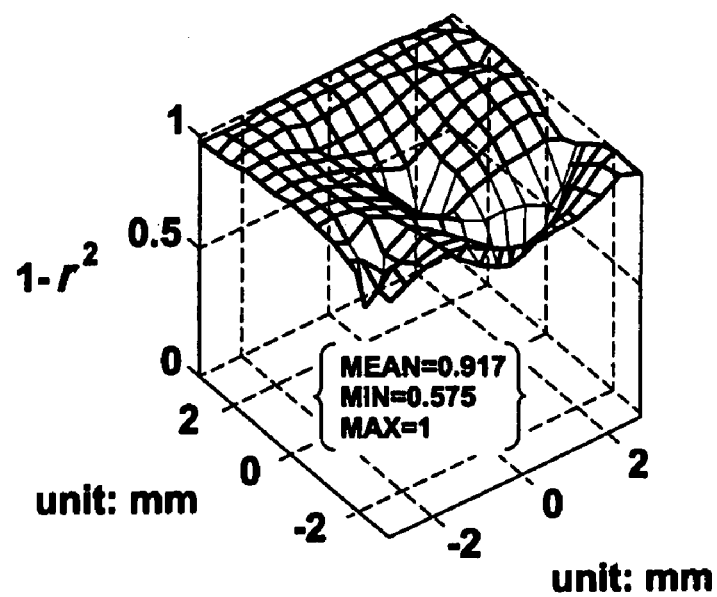
FIG. 7B is a plot that illustrates modified correlation coefficient analysis results of a reference chip and a thermally cycled chip.

FIG. 7A shows modified correlation coefficient (MCC) analysis results of two reference chips. The two chips are at the same location on two different panels. The mean value of $(1-r^2)$ is about 0.03, indicating strong linear relationship. FIG. 7B shows analysis results of a reference chip and a thermally cycled chip. The two chips are at the same location of two different panels. The mean value of $(1-r^2)$ in this case is 0.917, indicating that the signals from a reference (good) chip did not correlate well with the signals from a thermally cycled (cracked) chip. Furthermore, the maximum value of $(1-r^2)$ resulting from the comparisons between the reference chips is 0.197, which is much less than the minimum $(1-r^2)$ value of comparisons between a reference and a cracked chip. If, for instance, a user sets a threshold $(1-r^2)$ value equal to 0.4, then the quality of chip's solder joint connection can be checked by inspecting any point on the chip surface.

As explained above, in some embodiments, the inspection system 300 may make a determination, through user cooperation or automatically based on predefined criteria, whether to use a correlation coefficient, a modified correlation coefficient, an error ratio, and/or other methods. An error ratio method quantitatively identifies signal differences, and has an operation that includes integrating the total squared error between the waveforms and then normalizing this integrated value by one waveform chosen to be as reference. The equation is shown as follows:

$$ER = \frac{\int [f(t) - r(t)]^2 dt}{\int [r(t)]^2 dt}, \quad \text{Eq. 2}$$

where f(t) is the measured waveform, and r(t) is the reference waveform. Additional information about the ER method can be found in commonly assigned U.S. Pat. No. 6,747,268, herein incorporated by reference.

There are several factors to consider in choosing between an ER method versus, for example, a modified correlation coefficient (MCC) method. For example, the scale of the ER method generally depends on the device being tested. This limitation makes it difficult to set up a universal threshold ER value to separate defective samples from reference samples. Thus, the ER method should generally, though not necessarily, be used for relative comparisons between similar product types.

Another factor to consider is excitation laser power and its effect on the ER method as compared to the MCC method. The excitation laser power should be within a defined range. For example, in one embodiment, the excitation laser power generally should be high enough to generate measurable and less noisy vibration signals, but not too high to go beyond the thermoelastic regime and cause ablation. Note that the scope of the preferred embodiments may also be applied to some implementations that are not strictly non-destructive, such as when operating in the ablation regime. ER values can be affected by laser power fluctuation. For example, the surface displacement (e.g., vibration) waveform amplitude (such as those shown in FIG. 5) may increase with increasing excitation laser power, but the waveform shape change is minimal. Since the ER calculation uses integration of the amplitude differences, the amplitude change caused by laser power variation may change the ER. Because the laser power fluctuation causes little change in signal frequency and phase, a method such as the MCC method, which is insensitive to signal amplitude but is able to reflect the change of signal phase and frequency, may be better suited to minimize the effect of power fluctuation. Experiments show that when the laser power level is set between a range of approximately 50 mW and 70 mW, the MCC method allows a wider range of laser power variation than the ER method. Also, when the laser power is below approximately 40 mW, both the ER value and the MCC value increase and deviate from 0. Thus, to get comparable data, the laser power used in exciting both the reference chip and the defective chip should be kept in a range of about ±10 mW, which is a condition that can be met with a fixed laser attenuator setting.

Figure 8A:
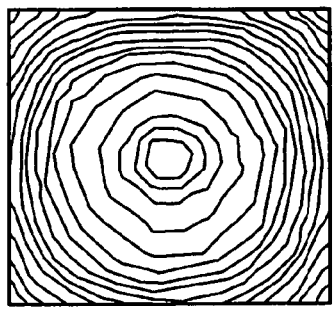
FIGS. 8A-8D are contour plots of surface vibration responses from a target object and a reference object.
Figure 8B:
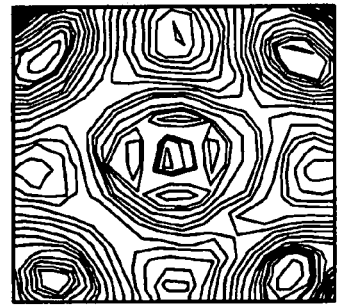
Figure 8C:
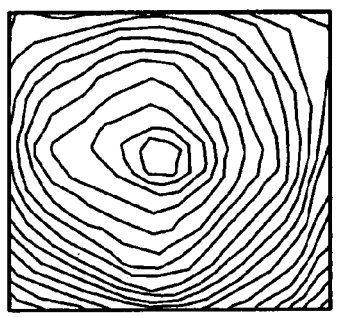
Figure 8D:
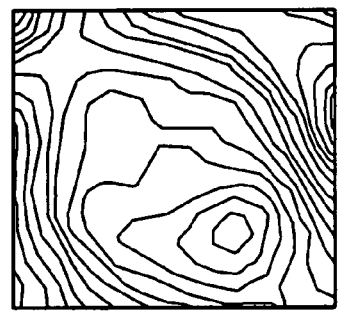

As explained above, embodiments of the inspection systems and methods can be implemented using two separate chips (a reference chip and a target chip, the target chip having a known defect in the solder joint and the reference chip(s) having "known good" solder joints) or a single chip (with both the reference signals and target signals derived from the same chip). In a test arrangement similar to that shown in FIG. 1, transient vibration responses of the whole chip surface were studied using a scanning pattern as described in association with FIG. 2. FIGS. 8A-8D show contour plots of the surface vibration responses. In particular, FIGS. 8A and 8B are contour plots derived from reference chips at two time instances, and FIGS. 8C and 8D are contour plots derived from object surfaces (at two time instances) that exhibited defects in the solder joints. As shown, the vibration responses of the reference chips show a circularly symmetric shape, but the responses of target chips (thermally cycled samples) show asymmetric twisting. If the chip's bumps are symmetrically distributed and the laser excitation point is located at a center of symmetry, and if all the solder joints are well-connected, then the response should show a symmetric shape as verified by the experimental data. The asymmetric response shape of the thermally cycled samples indicates weak solder joint connections at one or more locations. Based at least in part on this experimental observation, it is recognized that signals collected from symmetric locations on a single chip can be compared to evaluate the chip's solder joints. In particular, as long as the chip's bump locations are symmetrically distributed and the laser excitation point is located at the center of symmetry, the symmetry of the surface's vibration shape should reflect the quality of the solder joint connections.

ER methods, correlation coefficient methods, and MCC methods can be used to perform "auto-comparison" (i.e., comparing data from symmetric locations on the same chip). With regard to ER methods, an ER value may be affected by factors such as excitation laser power level, flip chip dimension and bump location, and/or solder joint quality. Thus, a "lower" ER value in one type of flip chip doesn't necessarily mean it is any better than a relatively "higher" ER value from another type of device. The comparison is relevant within the same type of device and using the same testing parameters, and that is one reason it is often difficult to configure a "universal" threshold with an ER method. Thus, an ER method may be used for auto-comparison since ER values can be calculated using signals on the same device and compared with a good device of the same design and using the same testing parameter.

Figure 9:
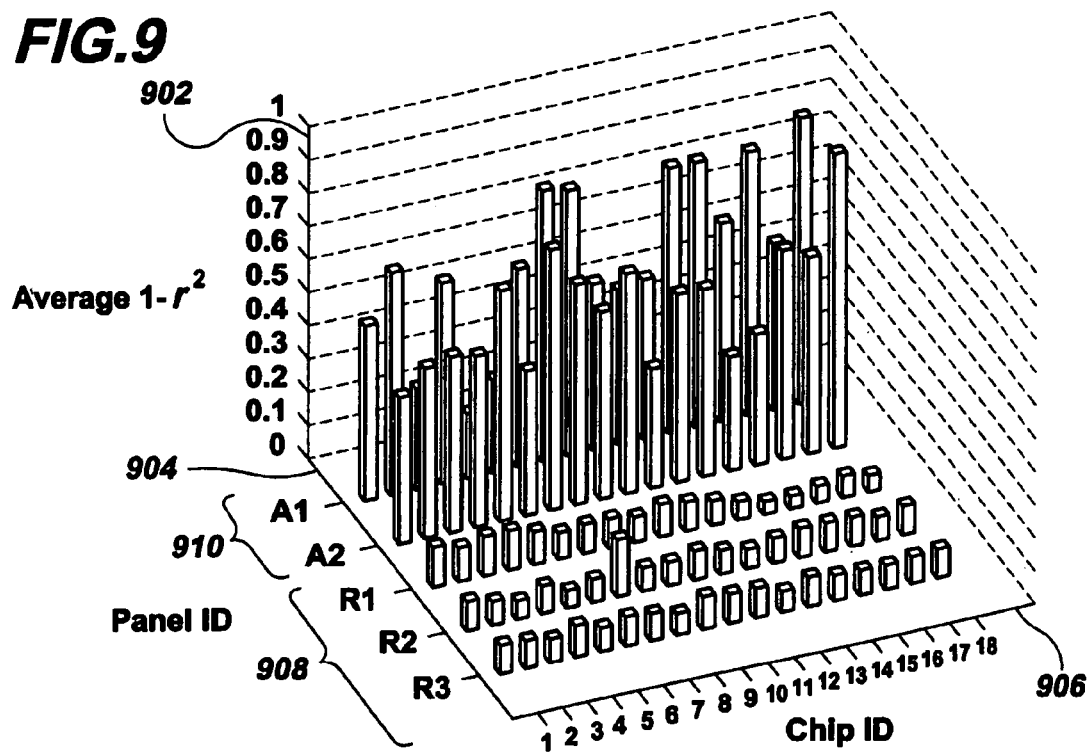
FIG. 9 is a plot that illustrates test results from an implementation of an embodiment of an auto-comparison method.

FIG. 9 shows the result of an auto-comparison method. The plot shows a first axis 902 corresponding to the average $(1-r^2)$ value, a second axis 904 corresponding to the panel identification (ID) (e.g., A1, A2, R1, R2, and R3), and a third axis 906 corresponding to the chip ID. Using a similar set-up to that discussed in association with FIG. 1, a total of 90 samples on five different panels were analyzed. For each sample chip, only four signals collected from the four corners of the chip were used for calculation. The signal detected from the lower left corner of the chip was compared with the one detected from the upper right corner, the signal detected from the lower right corner was compared with the one from the upper left corner, all using the MCC method. The two $(1-r^2)$ values were then averaged to give the final value for the test.

In FIG. 9, the three rows 908 in the front are the results for the chips located on panels R1, R2, and R3. They are all reference panels with good solder joint connections. The average values of MCC are all lower than 0.1 with only one exception (Chip 7 on panel R2). The two rows 910 in the back are the results for the chips located on panels A1 and A2. They are both thermally cycled panels. The values of MCC are much higher than those of the reference group. A threshold value of 0.2 for the MCC, for example, would thus successfully separate all the 36 chips with bad connections from the 54 well-connected chips. Thus, an auto-comparison using, for example, the MCC calculation can evaluate the chip's solder joint connection using only a few number (e.g., two) of symmetrically distributed inspection points, provided that the component shape and solder bump distribution have symmetry, and the laser excitation source is at the symmetry center. The use of auto-comparison eliminates the dependence on a known good reference, and can reduce the inspection time significantly. Note that auto-comparison is described using the MCC method, but the ER method as well as other methods can be used as well.

In light of the above disclosure, it is clear that another embodiment of an inspection method 300b, as illustrated in FIG. 10, comprises receiving a reference signal having first surface displacement information from a first location on an object (1002) and receiving a target signal having second surface displacement information from a second location on the object, the first location and the second location being symmetrical (or substantially similar) with respect to a reference point (e.g., the center where the laser impinges on the object) (1004). In 1006, a comparison is made between the first surface displacement information corresponding to the reference signal and the second surface displacement information corresponding to the target signal to determine whether the object is defective. If no defect is detected, the process (1002-1006) may begin again at additional symmetrical locations (1008) using the same reference point or a different reference point. The process may continue for subsequent locations until a defect is discovered or until a threshold number of locations have been evaluated. Alternatively, the process may end if no defect is detected after the first and second inspection locations provides no evidence of a defect. If a defect is detected, the process is completed and the object is flagged as defective (1010).

It should be emphasized that the above-described embodiments, particularly, any "preferred" embodiments, are merely possible examples of implementations, merely set forth for a clear understanding of the principles of the disclosed systems and methods. Many variations and modifications may be made to the above-described embodiment(s) without departing substantially from the principles of the disclosure. All such modifications and variations are intended to be included herein within the scope of this disclosure.

What is claimed is:
1. An inspection method, comprising:
receiving a reference signal having first surface displacement information, the first surface displacement information corresponding to a non-zero displacement of a first surface known in advance of inspection to have no defects;
receiving a target signal having second surface displacement information, the second surface displacement information corresponding to a non-zero displacement of a second surface;

determining a correlation coefficient between the first surface displacement information and the second surface displacement information, the correlation coefficient determined according to an equation for r, wherein the equation comprises:

$$r = \frac{\sum_n (R_n - \overline{R})(A_n - \overline{A})}{\sqrt{\left(\sum_n (R_n - \overline{R})^2\right)\left(\sum_n (A_n - \overline{A})^2\right)}}$$

where $R_n$ corresponds to the first surface displacement information, $\overline{R}$ corresponds to a mean of $R_n$, $A_n$ corresponds to the second surface displacement information, and $\overline{A}$ is a mean of $A_n$;

determining a modified correlation coefficient, the modified correlation coefficient equal to $(1-r^2)$;

comparing the determined modified correlation coefficient with a threshold modified correlation coefficient; and indicating whether the inspected object exhibits a defect based on the comparison between the determined modified correlation coefficient and the threshold modified correlation coefficient.

2. The method of claim 1, wherein receiving the reference signal comprises receiving the reference signal derived from detecting the first surface displacement information from the inspected object located on a printed circuit board.

3. The method of claim 1, wherein receiving the reference signal comprises receiving the reference signal derived from detecting the first surface displacement information from a reference object that is located on a printed circuit board distinct from a printed circuit board comprising the inspected object.

4. The method of claim 1, further comprising determining an error ratio between the first surface displacement information and the second surface displacement information, the error ratio indicating whether the inspected object exhibits a defect.

5. An inspection system, comprising:

logic configured to receive a reference signal and a target signal, the reference signal having first surface displacement information and the target signal having second surface displacement information, the first surface displacement information corresponding to a non-zero displacement of a first surface known in advance of inspection to have no defects, the second surface displacement information corresponding to a non-zero displacement of a second surface, said logic further configured to:

determine a correlation coefficient between the first surface displacement information and the second surface displacement information, the correlation coefficient determined according to an equation for r, wherein the equation comprises:

$$r = \frac{\sum_n (R_n - \overline{R})(A_n - \overline{A})}{\sqrt{\left(\sum_n (R_n - \overline{R})^2\right)\left(\sum_n (A_n - \overline{A})^2\right)}}$$

where $R_n$ corresponds to the first surface displacement information, $\overline{R}$ corresponds to a mean of $R_n$, $A_n$ corresponds to the second surface displacement information, and $\overline{A}$ is a mean of $A_n$; and indicate whether an inspected object exhibits a defect based on a value of the correlation coefficient.

6. The system of claim 5, wherein the logic is further configured to receive the reference signal from the inspected object located on a printed circuit board.

7. The system of claim 5, wherein the logic is further configured to receive the reference signal from a reference object that is located on a printed circuit board distinct from a printed circuit board comprising the inspected object.

8. The system of claim 5, wherein the logic is further configured to determine an error ratio between the first surface displacement information and the second surface displacement information, the error ratio indicating whether the inspected object exhibits a defect.

9. The system of claim 5, wherein the logic is further configured to present a user with an ability to choose at least one comparison method among a plurality of comparison methods to compare the first surface displacement information and the second surface displacement information.

10. The system of claim 5, wherein the logic is further configured to automatically determine at least one comparison method among a plurality of comparison methods to use to compare the first surface displacement information and the second surface displacement information.

11. The system of claim 5, wherein the correlation coefficient includes a modified correlation coefficient, the modified correlation coefficient equal to $(1-r^2)$.

12. The system of claim 5, further comprising a processor configured to execute the logic.

13. The system of claim 5, wherein the logic comprises at least one of hardware and software.

14. An inspection system, comprising:

means for receiving a reference signal having first surface displacement information, the first surface displacement information corresponding to a non-zero displacement of a first surface known in advance of inspection to have no defects;

means for receiving a target signal having second surface displacement information, the second surface displacement information corresponding to a non-zero displacement of a second surface; and means for:

determining a correlation coefficient between the reference signal and the target signal, the correlation coefficient determined according to an equation for r, wherein the equation comprises:

$$r = \frac{\sum_n (R_n - \overline{R})(A_n - \overline{A})}{\sqrt{\left(\sum_n (R_n - \overline{R})^2\right)\left(\sum_n (A_n - \overline{A})^2\right)}}$$

where $R_n$ corresponds to the first surface displacement information, $\overline{R}$ corresponds to a mean of $R_n$, $A_n$ corresponds to the second surface displacement information, and $\overline{A}$ is a mean of $A_n$;

determining a modified correlation coefficient, the modified correlation coefficient equal to $(1-r^2)$;

comparing the determined modified correlation coefficient with a threshold modified correlation coefficient; and indicating whether the inspected object exhibits a defect based on the comparison between the determined modified correlation coefficient and the threshold modified correlation coefficient.

15. A computer-readable medium having a computer program for inspecting an object, the computer-readable medium comprising:
- logic configured to receive a reference signal having first surface displacement information, the first surface displacement information corresponding to a non-zero displacement of a first surface known in advance of inspection to have no defects;
- logic configured to receive a target signal having second surface displacement information, the second surface displacement information corresponding to a non-zero displacement of a second surface; and
- logic configured to determine a correlation coefficient between the reference signal and the target signal, the correlation coefficient determined according to an equation for r, wherein the equation comprises:

$$r = \frac{\sum_n (R_n - \overline{R})(A_n - \overline{A})}{\sqrt{\left(\sum_n (R_n - \overline{R})^2\right)\left(\sum_n (A_n - \overline{A})^2\right)}}$$

where $R_n$ corresponds to the first surface displacement information, $\overline{R}$ corresponds to a mean of $R_n$, $A_n$ corresponds to the second surface displacement information, and $\overline{A}$ is a mean of $A_n$;
- logic configured to determine a modified correlation coefficient, the modified correlation coefficient equal to $(1-r^2)$;
- logic configured to compare the determined modified correlation coefficient with a threshold modified correlation coefficient; and
- logic configured to indicate whether an inspected object exhibits a defect based on the comparison between the determined modified correlation coefficient and the threshold modified correlation coefficient.

16. An auto comparison method, comprising:
- receiving a reference signal having first surface displacement information from a first location on an object;
- receiving a target signal having second surface displacement information from a second location on the object, the first location and the second location being substantially symmetrical with respect to a reference point;
- comparing the reference signal and the target signal to determine whether the object is defective; and
- indicating whether the object is defective.

17. The method of claim 16, wherein comparing comprises performing at least one of a correlation coefficient method, an error ratio method, frequency-domain spectral analysis method, and defect pattern recognition method.

18. The method of claim 17, wherein the correlation coefficient includes a modified correlation coefficient.

19. An auto comparison system, comprising: logic configured to receive a reference signal having first surface displacement information from a first location on an object, receive a target signal having second surface displacement information from a second location on the object, the first location and the second location being substantially symmetrical with respect to a reference point, and compare the reference signal and the target signal to determine whether the object is defective.

20. The system of claim 19, wherein when the logic is comparing, the logic is configured to perform at least one of a correlation coefficient method, an error ratio method, frequency-domain spectral analysis method, and defect pattern recognition method.

21. The system of claim 19, wherein the correlation coefficient includes a modified correlation coefficient.

22. The system of claim 19, wherein the logic comprises at least one of software and hardware.

* * * * *